US011156597B2

(12) United States Patent
Qin

(10) Patent No.: US 11,156,597 B2
(45) Date of Patent: Oct. 26, 2021

(54) URINE TESTING DEVICE AND SMART TOILET COMPRISING SAME

(71) Applicant: Shanghai Kohler Electronics, Ltd., Shanghai (CN)

(72) Inventor: Zhiyu Qin, Beijing (CN)

(73) Assignee: Shanghai Kohler Electronics, Ltd., Shanghai (CN)

( * ) Notice: Subject to any disclaimer, the term of this patent is extended or adjusted under 35 U.S.C. 154(b) by 385 days.

(21) Appl. No.: 16/099,642

(22) PCT Filed: Oct. 25, 2016

(86) PCT No.: PCT/CN2016/103191
§ 371 (c)(1),
(2) Date: Nov. 7, 2018

(87) PCT Pub. No.: WO2017/193543
PCT Pub. Date: Nov. 16, 2017

(65) Prior Publication Data
US 2019/0170728 A1 Jun. 6, 2019

(30) Foreign Application Priority Data
May 10, 2016 (CN) .......................... 201610305770.6

(51) Int. Cl.
*G01N 33/493* (2006.01)
*G01N 33/50* (2006.01)
(Continued)

(52) U.S. Cl.
CPC ........... *G01N 33/493* (2013.01); *A61B 5/207* (2013.01); *A61B 10/007* (2013.01); *G01N 1/10* (2013.01);
(Continued)

(58) Field of Classification Search
CPC ........ G01N 33/493; G01N 33/50; G01N 1/10; G01N 35/00871; G01N 1/20; G01N 35/10;
(Continued)

(56) References Cited

U.S. PATENT DOCUMENTS 4,943,416 A * 7/1990 Kikuchi ............... G01N 33/493
422/63
2012/0162653 A1* 6/2012 Lee ..................... G01N 21/8483
356/436

FOREIGN PATENT DOCUMENTS

| CN | 101887065 | 11/2010 |
| CN | 104155437 | 11/2014 |

(Continued)

OTHER PUBLICATIONS

International Search Report re Application No. PCT/CN2016/103191; 6 pgs.

*Primary Examiner* — Jill A Warden
*Assistant Examiner* — Henry H Nguyen
(74) *Attorney, Agent, or Firm* — Foley & Lardner LLP

(57) ABSTRACT

A urine testing device and a smart toilet having the urine testing device, which includes a base, a paper feeding module, a sample adding module, and a testing module installed on the base and arranged in a linear form. The paper feeding module has a test paper box, a lifting mechanism, and a pushing mechanism. A horizontal paper leakage groove is disposed at a bottom of the test paper box to receive a bottommost piece of test paper. The lifting mechanism lifts and descends the test paper box to reveal/seal the paper leakage groove. The pushing mechanism pushes out test paper from the paper leakage groove and delivers test paper to the sample adding and testing modules. The sample adding module dropwise adds urine to be tested on test (Continued)

paper. The testing module tests test paper added with the sample to obtain a urine testing result.

16 Claims, 5 Drawing Sheets

(51) Int. Cl.
    *G01N 35/10*     (2006.01)
    *G01N 33/487*     (2006.01)
    *A61B 5/20*     (2006.01)
    *A61B 10/00*     (2006.01)
    *G01N 1/10*     (2006.01)
    *G01N 35/00*     (2006.01)
    *E03D 9/00*     (2006.01)

(52) U.S. Cl.
    CPC ......... *G01N 33/4875* (2013.01); *G01N 33/50* (2013.01); *G01N 35/10* (2013.01); *G01N 35/1004* (2013.01); *A61B 2562/0295* (2013.01); *E03D 9/00* (2013.01); *E03D 2201/00* (2013.01); *G01N 35/00871* (2013.01)

(58) Field of Classification Search
    CPC ............ G01N 35/1004; G01N 33/4875; A61B 10/007; A61B 5/207; A61B 2562/0295; E03D 2201/00; E03D 9/00
    See application file for complete search history.

(56) References Cited

FOREIGN PATENT DOCUMENTS

| | | |
|---|---|---|
| CN | 104483499 | 4/2015 |
| CN | 104790487 | 7/2015 |
| CN | 105738609 | 7/2016 |
| CN | 205643354 | 10/2016 |
| WO | WO2014121699 | 8/2014 |

\* cited by examiner

URINE TESTING DEVICE AND SMART TOILET COMPRISING SAME

CROSS-REFERENCE TO RELATED PATENT APPLICATIONS

This application is a national stage of International Application No, PCT/CN2016/103191, filed Oct. 25, 2016, which claims the benefit and priority of Chinese Patent Application No. 201610305770.6, filed May 10, 2016, both of which are incorporated herein by reference in their entireties.

TECHNICAL FIELD

The present invention relates to the field of household health care or medical instrument, and more particularly, to a urine testing device and a smart toilet comprising same.

BACKGROUND

With the improvement of people's life demands, smart toilets are increasingly favored by the consumer. Currently, the smart toilets generally have the functions of cleaning, heating, sterilizing, or the like, but rarely have the urine testing function. Most of the existing urine testing devices are large medical instruments. During testing, the test paper is usually vertical to a pushing direction of a machine, a mechanical device pushes the test paper below a sample adding needle, the sample adding needle moves in a direction parallel to the test paper and dropwise adds samples, and then the mechanical device continues to push the test paper to a photoelectric detection position. A photoelectric probe moves in a direction parallel to the test paper and reads the results, and the mechanical device continues to push the test paper to a waste paper box. A system designed in this way has a very fast testing speed, but is not compact enough in structure, and has a larger space volume, which is not suitable to an occasion such as the smart toilet, which needs a compact structure, has heavy environmental humidity, and does not need fast testing speed.

SUMMARY

One object of the present invention is to provide a urine testing device that has a small volume and a compact structure, is easy in installation and reliable in operation, and is more suitable for being installed in a smart toilet for use.

Another object of the present invention is to provide a smart toilet containing the urine testing device above.

In order to achieve the objects above, the following technical solutions are adopted in the present invention.

A urine testing device comprises a base, and a paper feeding module, a sample adding module and a testing module installed on the base and compactly arranged in a linear form from left to right, wherein: the paper feeding module comprises a test paper box, a lifting mechanism, and a pushing mechanism, a horizontal paper leakage groove is disposed at a bottom of the test paper box, and is used for receiving a bottommost piece of test paper which drops down by dead weight; the lifting mechanism is used for lifting and descending the test paper box to reveal or seal the paper leakage groove; the pushing mechanism is used for pushing out the test paper from the paper leakage groove and delivering the test paper to the sample adding module and the testing module; the sample adding module is used for dropwise adding urine to be tested on the test paper; and the testing module is used for testing the test paper added with the sample to obtain a urine testing result.

As a further improvement, the base is an integrated base, the base is respectively provided with an installation area for the paper feeding module, an installation area for the sample adding module and an installation area for the testing module, the installation area for the paper feeding module is provided with a containing cavity for installing the test paper box, a paper guide table is disposed at a right side of the containing cavity, and a test paper translation channel on the base is disposed at a right side of the paper guide table.

A bottom of the containing cavity is provided with a groove used for embedding the paper leakage groove, and an opening of the groove is provided with a sealing gasket for sealing the paper leakage groove.

The lifting mechanism comprises a first motor and a lifting snap table, the lifting snap table is installed in the containing cavity, the test paper box is snap-fit into the lifting snap table, and the first motor is connected to the lifting snap table and drives the lifting snap table to lift and descend, so as to drive the test paper box to lift and descend.

The pushing mechanism comprises a second motor, a pulling rod connected to the second motor, a third motor, and a screw rod connected to the third motor, the second motor is fixedly installed in a platform, the platform is sheathed on the screw rod and is internally provided with an internal thread matched with the screw rod, when the third motor drives the screw rod to rotate, the platform translates along the screw rod to drive the pulling rod to translate, the second motor is used for driving the pulling rod to an initial position or a working position, and the working position of the puling rod is aligned with the paper leakage groove.

The sample adding module comprises a fourth motor and a sample adding needle, the sample adding needle is used for being connected to a sample feeder, and the fourth motor is connected to the sample adding needle and drives the sample adding needle to move to a sample adding position or a cleaning position.

The sample feeder comprises a liquid inlet tube and a plunger pump, the liquid inlet tube is connected to the sample adding needle, the plunger pump is used for being respectively connected to a urine-collecting pipeline and a cleaning pipeline; during testing, the sample adding needle moves to the sample adding position, and the plunger pump is used for pumping the urine to be tested from the urine-collecting pipeline to the sample adding needle through the liquid inlet tube; and after testing, the sample adding needle moves to the cleaning position, and the plunger pump is used for pumping a cleaning fluid from the cleaning pipeline to the sample adding needle through the liquid inlet tube.

The testing module comprises a photoelectric probe detector, the photoelectric probe detector comprises a support installed on the base and multiple sets of photoelectric probes disposed in the support side by side, and each set of photoelectric probes is used for correspondingly testing one testing area on the test paper to be tested.

The testing module further comprises a fifth motor, the fifth motor is connected to the photoelectric probe detector and drives the photoelectric probe detector to move to a calibrating position, a testing position or a test paper recycling position, and a separable test paper recycling box is disposed below a position of the base corresponding to the test paper recycling position of the photoelectric probe detector.

A smart toilet comprises the urine testing device.

By adopting the technical solutions above, the present invention at least has the following advantages.

(1) Since the test paper box provided with the horizontal paper leakage groove at the bottom thereof is used, and matched with the lifting mechanism and the pushing mechanism, the horizontally placed test paper leaks out automatically by dead weight, and the test paper is easy to be movably pushed in a horizontal direction, thereby laying the foundation for the layout and working mode of the subsequent sample adding module and the testing module.

(2) Because the test paper is parallel to the pushing direction, the paper feeding module, the sample adding module and the testing module can be compactly arranged on the base in a linear form, so as to realize the modular setting with reasonable layout and high space utilization, and the urine testing process is finished at one time on the base from left to right; when each module implements the test, the movement range and the occupied space are small.

(3) Since the groove and the sealing gasket are disposed, sealing can be ensured when the lifting mechanism descends the test paper box, and the test paper box is not easy to be affected with damp and invalid during storage, so that when the test paper box is applied to the smart toilet, the test paper box is prevented from being affected by damp environment of toilet.

(4) Because the sample adding module is provided with the working position and the cleaning position of the sample adding needle, the cleaning is timely conducted after finishing the urine test, so as to avoid mutual effect between two tests.

(5) Since the photoelectric probe detector comprises multiple sets of photoelectric probes disposed side by side, when the test paper is translated below the photoelectric probe, the multiple sets of photoelectric probes work simultaneously, the test work of multiple test areas on the test paper can be finished at one time, comparing with traditional single-probe mobile scanning, the test efficiency is improved, the work mode of the detector is simplified, and the occupied space is saved.

BRIEF DESCRIPTION OF THE FIGURES

The foregoing description is merely a summary of the technical solutions of the present invention. To understand the technical means of the present invention more clearly, the present invention is further described in detail with reference to the figures and the detailed embodiments hereinafter.

DETAILED DESCRIPTION

The present invention provides a urine testing device and a smart toilet comprising same. The urine testing device has a small volume and a compact structure, and is easy in installation and reliable in operation, and the smart toilet comprising same can conduct health data analysis to a urine sample collected, so that the smart toilet realizes a urine analysis function as a health care instrument.

The urine testing device according to the present invention comprises a base, and a paper feeding module, a sample adding module and a testing module installed on the base and compactly arranged in a linear form from left to right. The paper feeding module comprises a test paper box, a lifting mechanism, and a pushing mechanism, a horizontal paper leakage groove is disposed at a bottom of the test paper box, and is used for receiving a bottommost piece of test paper which drops down by dead weight; the lifting mechanism is used for lifting and descending the test paper box to reveal or seal the paper leakage groove; the pushing mechanism is used for pushing out the test paper from the paper leakage groove and delivering the test paper to the sample adding module and the testing module; the sample adding module is used for dropwise adding urine to be tested on the test paper; and the testing module is used for testing the test paper added with the sample to obtain a urine testing result.

Figure 1:
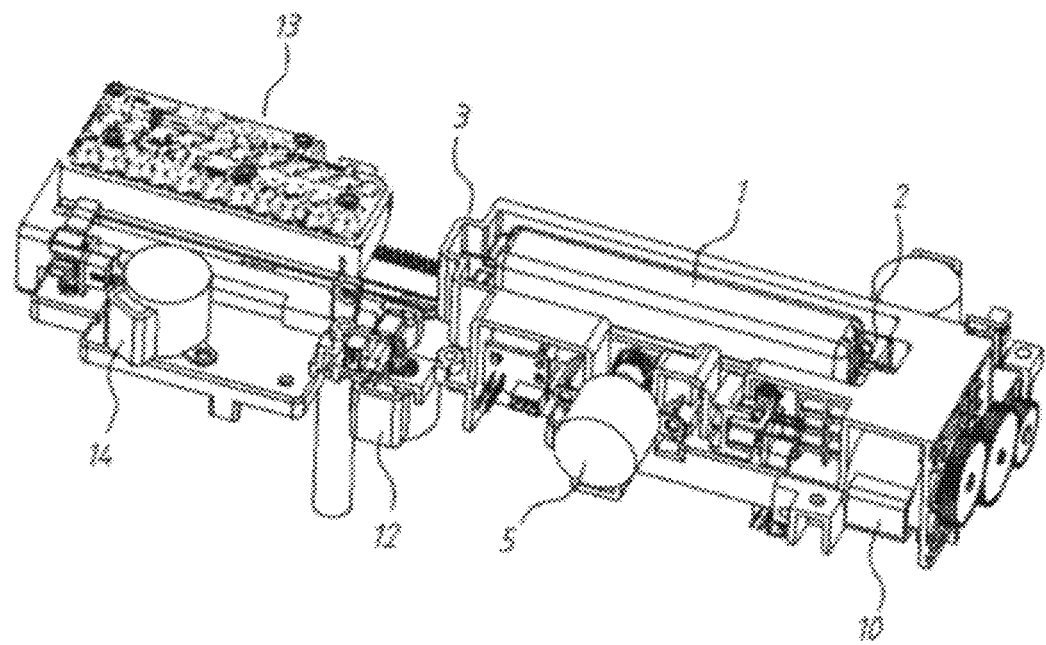
FIGS. 1 and 2 are respectively schematic structure diagram of a urine testing device at different angles according to the present invention.
Figure 2:
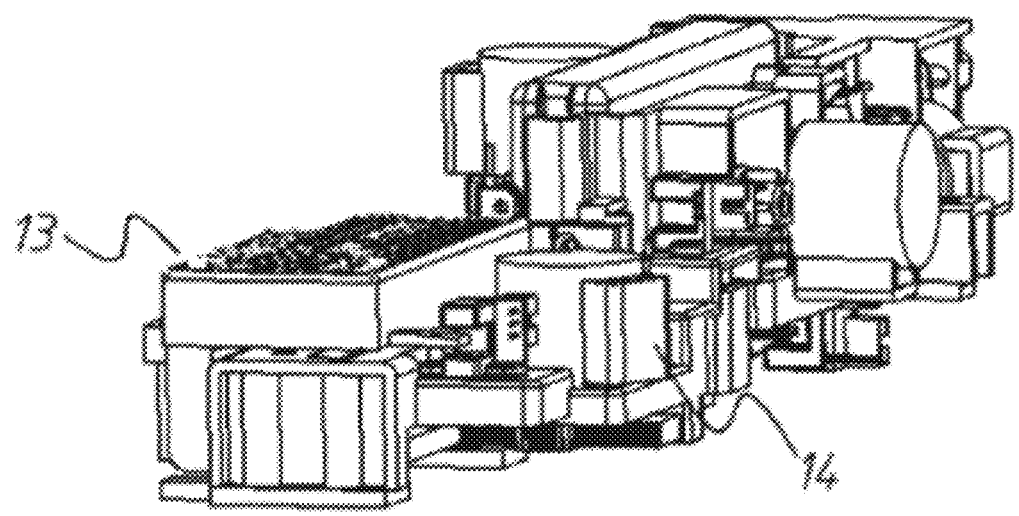
Figure 3:
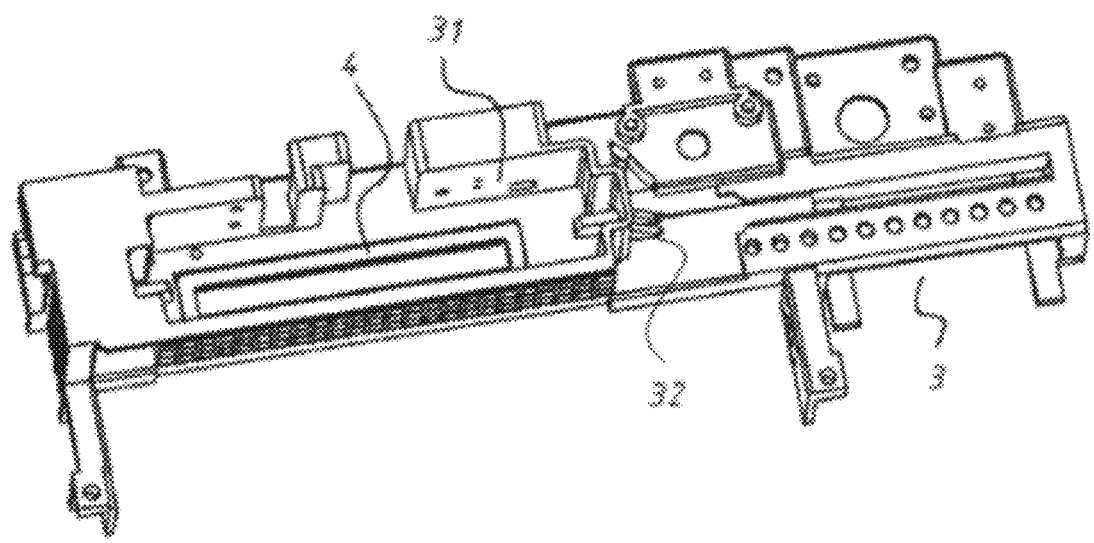
FIG. 3 is a schematic structure diagram of an integrated base.

Specifically, with reference to FIGS. 1, 2 and 3, the base 3 is an integrated base, the base 3 is respectively provided with an installation area for the paper feeding module, an installation area for the sample adding module and an installation area for the testing module, wherein the installation area for the paper feeding module is provided with a containing cavity 31 for installing the test paper box 1, a paper guide table 32 is disposed at a right side of the containing cavity 31, and a test paper translation channel on the base 3 is disposed at a right side of the paper guide table 32.

Figure 4:
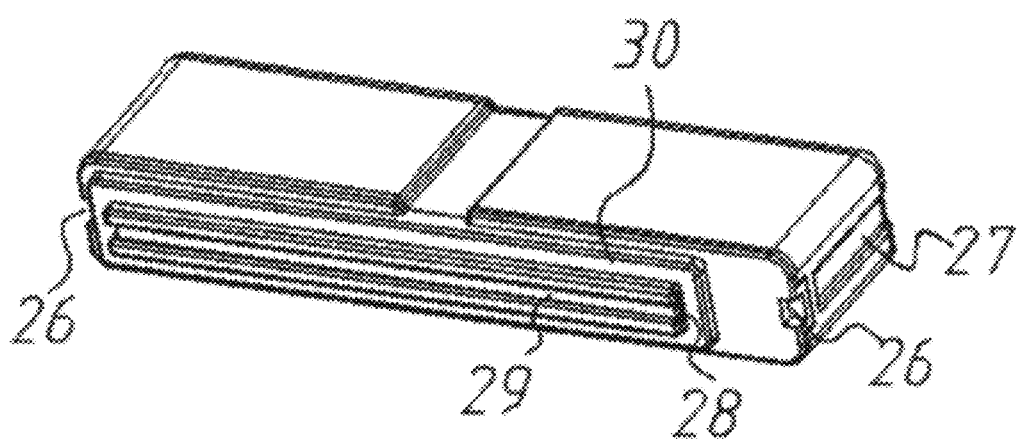
FIG. 4 is a schematic structure diagram of a test paper box.

With reference to FIGS. 3 and 4, the test paper box 1 is used for placing the test paper for testing, the test paper is in an elongated shape, and is provided with multiple testing areas, which are respectively used for testing different index parameters of the urine. A plurality of elongated test papers are stacked one on another in the test paper box 1 for continuous testing. A bottom of the test paper box 1 is provided with a horizontal paper leakage groove 29, the paper leakage groove 29 is in an elongate shape, and is matched with the shape of the test paper placed in the test paper box 1, a bottommost piece of test paper drops down into the paper leakage groove 29 by dead weight, and a right end of the paper leakage groove 29 is a test paper outlet 28. A bottom of the containing cavity 31 is provided with a groove used for embedding the paper leakage groove 29, an opening of the groove is provided with a sealing gasket 4, and preferably, an upper surface of the sealing gasket 4 is flush with or a little sunk to the opening of the groove, thereby avoiding the situation that it prevents a pulling rod of the pushing mechanism from pushing in a subsequent action. A bottom of the test paper box 1 is provided with a seal platform 30, the seal platform 30 is set as a bulge surrounding the periphery of the paper leakage groove 29, and the seal platform 30 is matched with the sealing gasket 4 for sealing the paper leakage groove 29 under a non-test state, so as to prevent the test paper in the test paper box 1 from being invalid after being affected with damp.

Figure 5:
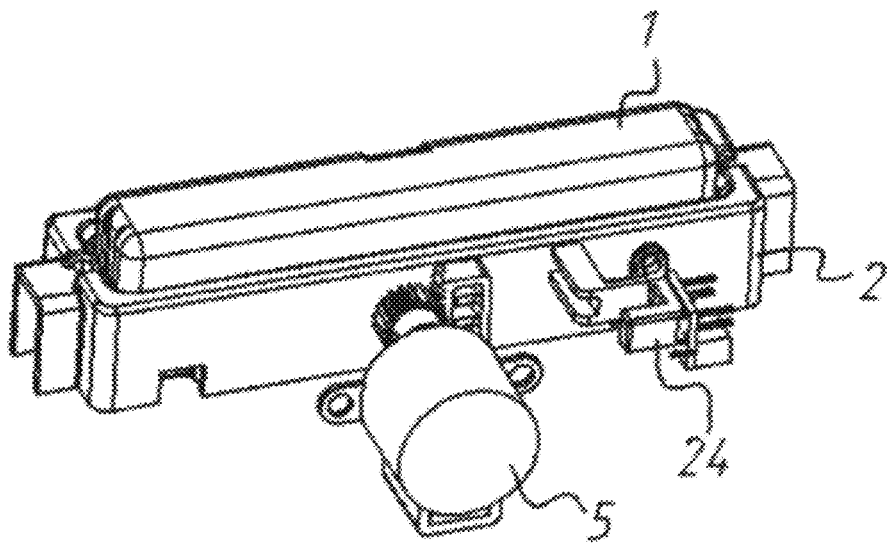
FIG. 5 is a schematic structure diagram of a lifting mechanism.
Figure 6:
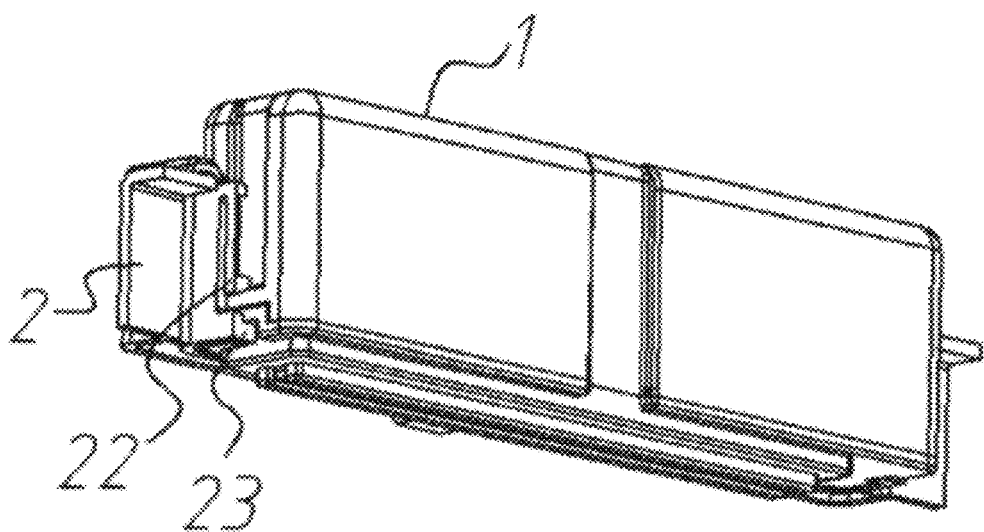
FIG. 6 is a schematic diagram illustrating matching structures of a lifting snap table and the test paper box.

With reference to FIGS. 4 and 5, two sides of the body of the test paper box 1 are respectively provided with two grooves, comprising upper grooves 27 and lower grooves 26, the lifting mechanism comprises a first motor 5 and a lifting snap table 2, the lifting snap table 2 is installed in the containing cavity 31, the test paper box 1 is snap-fit into the lifting snap table 2 through the upper grooves 27 and the lower grooves 26, and specifically, as shown in FIG. 6, left and right sides of the lifting snap table 2 have two bosses 23, the lower grooves 26 at the bottom of the test paper box 1 are supported on the bosses 23, the left and right sides of the lifting snap table 2 further have two buckles 22, the buckles 22 are pressed on the upper grooves 27 at left and right sides of the test paper box 1, and the test paper box 1 is snap-fit into the lifting snap table 2. As shown in FIG. 5, a rack structure is disposed behind the lifting snap table 2, which is matched with a gear on a main shaft of the first motor 5 to form a drive mechanism, and the first motor 5 can drive the lifting snap table 2 to lift and descend in the containing cavity 31. A zero point of the lifting table 2 is determined by an optocoupler 24, under a non-test state, the lifting table 2 is located at the zero point, the test paper box 1 is tightly pressed on the sealing gasket 4, and an interior of the test paper box 1 is in a sealed state. When starting testing, the motor 5 drives the lifting snap table 2 to move upwardly, and the test paper box 1 moves upwardly, until a bottom surface of the test paper box 1 is higher than the groove at the bottom of the containing cavity 31. A bottommost piece of test paper in the paper leakage groove of the test paper box 1 is revealed, and the action of the lifting mechanism is stopped to wait for the pushing mechanism to push.

Figure 7:
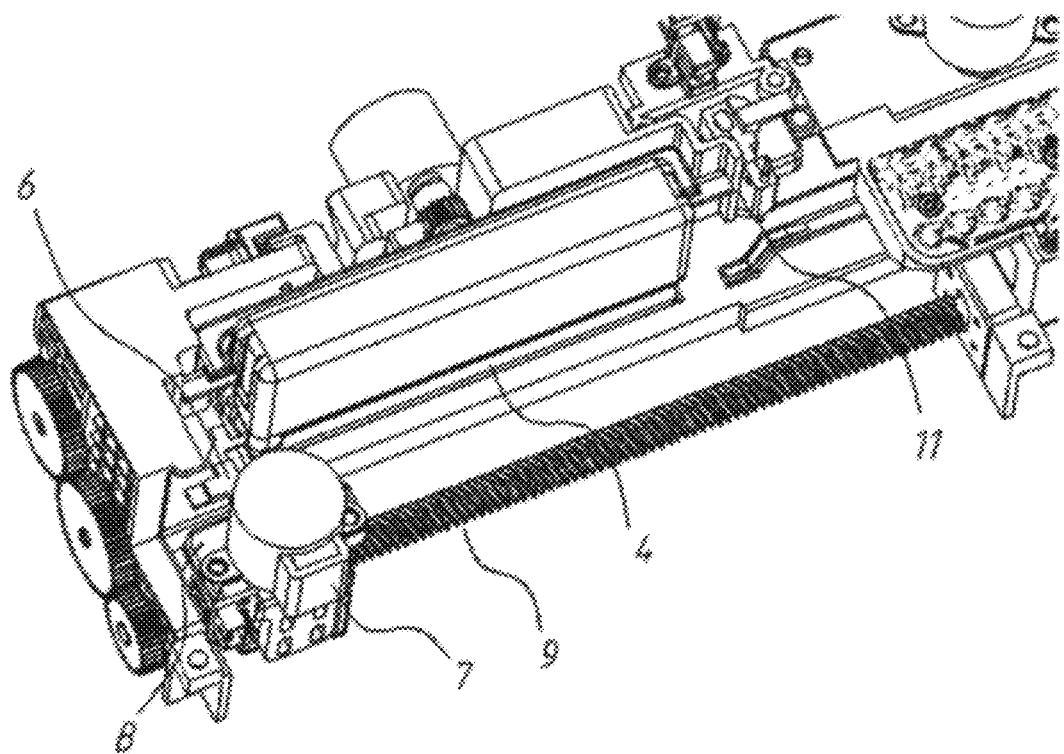
FIG. 7 is a partial schematic structure diagram (comprising partial section view) of the urine testing device according to the present invention.
Figure 8:
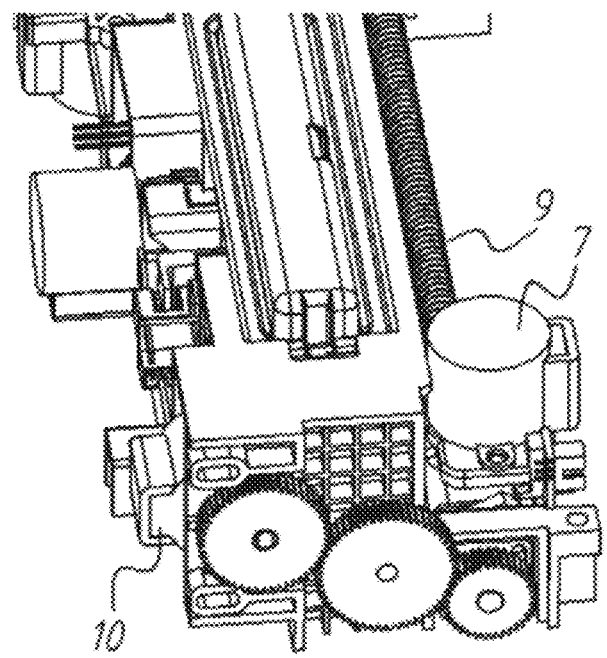
FIG. 8 is a partial schematic structure diagram of a pushing mechanism.

With reference to FIGS. 7 and 8, the pushing mechanism comprises a second motor 7, a pulling rod 6 connected to and driven by the second motor 7, a third motor 10, and a screw rod 9 connected to and driven by the third motor 10, the second motor 7 is fixedly installed in a platform 8, the platform 8 is sheathed on the screw rod 9 and is internally provided with an internal thread matched with an external thread of the screw rod 9, the third motor 10 drives the screw rod 9 to rotate through the gear, when the screw rod 9 rotates, the platform 8 is driven to translate along the screw rod 9, and the second motor 7 installed in the platform 8 drives the pulling rod 6 to translate. The pulling rod 6 is connected to a main shaft of the second motor 7, is driven by the second motor 7, and can be switched between a pushing position and an initial position. Under a non-test state, the pulling rod 6 is located at the initial position. When starting testing, the test paper box 1 is lifted by the lifting mechanism, and is stopped when the paper leakage groove 29 is on an upper surface of the pulling rod 6, to wait for the pulling rod 6 to push the test paper forwardly. The pulling rod 6 swings to the pushing position (working position) and follows the platform 8 to push out the test paper from the outlet 28 of the paper leakage groove 29, and then the test paper moves along a translation channel on the base 3 after being connected by a paper guide table, and stops until the test paper is pushed below the sample adding module to wait for the sample adding module to add sample.

Figure 9:
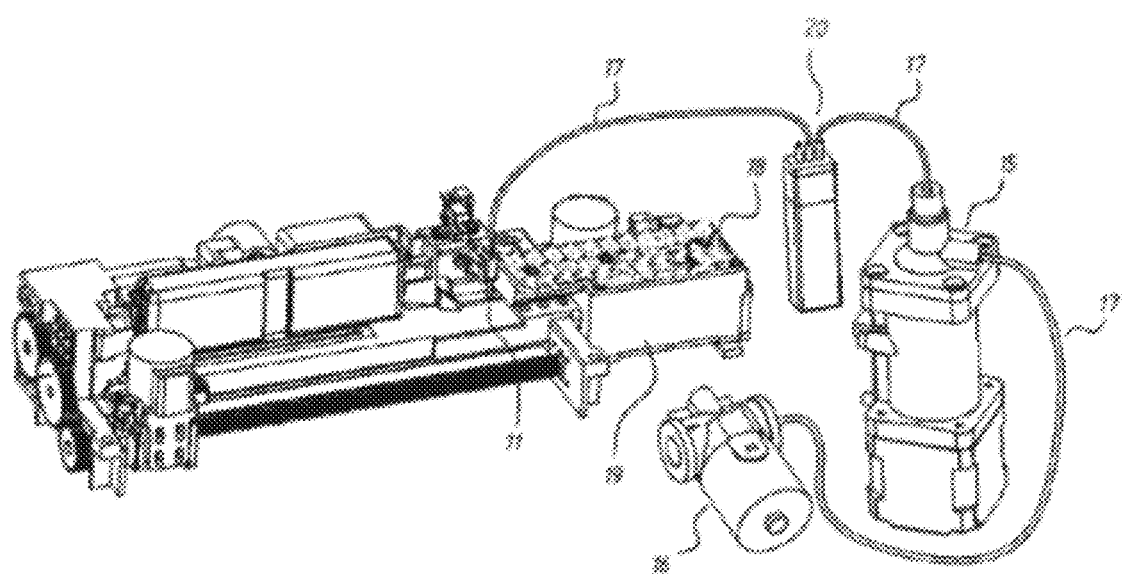
FIG. 9 is a schematic structure illustrating connection between a sample feeder and a sample adding module.

With reference to FIGS. 1, 7 and 9, the sample adding module comprises a fourth motor 12 and a sample adding needle 11, and the sample adding needle 11 is connected to a main shaft of the fourth motor 12, is driven by the fourth motor 12, and can be switched between a sample adding position (working position) and a cleaning position. When the urine testing device is applied to a smart toilet, the sample adding needle 11 is used for being connected to a sample feeder, the sample feeder comprises a liquid inlet tube and a plunger pump, the liquid inlet tube is connected to the sample adding needle 11, and the plunger pump is used for being respectively connected to a urine-collecting pipeline and a cleaning pipeline. As a specific example, as shown in FIG. 9, the sample adding device comprises a plunger pump 15, a three-way magnetic valve 20, a magnetic valve 16, and a hose 17, three valve ports of the three-way magnetic valve are respectively connected to the plunger pump 15, the sample adding needle 11 and the urine-collecting pipeline (not shown in the figure) through the hose 17, the plunger pump 15 is further connected to the cleaning pipeline through the hose 17, and the cleaning pipeline is provided with the magnetic valve 16. Under a non-test state, the sample adding needle 11 is located at the cleaning position. When the test is started, the sample adding needle 11 is moved to the working position, the plunger pump 15 pumps the urine to be tested from the urine-collecting pipeline to the sample adding needle 11 through the hose 17, and after the test paper reaches below the sample adding needle 11, the sample adding needle 11 starts to spit liquid. After the sample is dropwise added to the test paper, the sample adding needle 11 swings back to the cleaning position, the plunger pump 15 pumps a cleaning fluid from the cleaning pipeline to the sample adding needle 11 through the hose 17, and after the cleaning is finished, the magnetic valve 16 is closed. Wherein, a plastic hose can be used as the hose 17, and tap water can be directly used as the cleaning fluid.

With reference to FIGS. 1, 2 and 9, the testing module comprises a photoelectric probe detector 13 installed on the base 3, and a fifth motor 14 that is connected to the photoelectric probe detector 13 and drives the photoelectric probe detector 13 to move. The photoelectric probe detector 13 comprises a support 19 and a testing circuit 18 installed in the support 19, the testing circuit 18 comprises multiple sets of photoelectric probes disposed side by side, and each set of photoelectric probes is used for correspondingly testing one testing area on the test paper to be tested. The fifth motor 14 is connected to the support 19 and drives the support 19 to move, so that the photoelectric probe detector 13 is switched among a testing position, a test paper recycling position, and a calibrating position. Under a non-test state, the photoelectric probe detector 13 is located at the test paper recycling position. When the test is started, the photoelectric probe detector 13 enters the calibrating position to calibrate a sensor. After the sensor is calibrated, the photoelectric probe detector 13 enters the testing position. When the pulling rod 6 continuously pushes the test paper to be translated below the photoelectric probe of the photoelectric probe detector 13, the multiple sets of photoelectric probes start to read the result. A separable test paper recycling box is disposed below a position of the base 3 corresponding to the test paper recycling position of the photoelectric probe detector 13, when the result is read, the photoelectric probe detector 13 returns to the test paper recycling position, and the test paper drops into the test paper recycling position below.

When the urine is tested by the urine testing device of the present invention, the sample is added while the paper is pushed out, and the test paper enters below the photoelectric probe after being dropwise added with the sample. After the test paper is pushed below the photoelectric probe, the pulling rod 6 swings back to the initial position, the platform 8 returns to a left-most side of a bracket 3, the sample adding needle 11 swings back to the cleaning position, the magnetic valve 16 is opened, the plunger pump 15, the sample adding needle 11 and the hose 17 are cleaned by tap water, and after cleaning, the magnetic valve 16 is closed.

The foregoing description is merely preferred embodiments of the present invention, but is not intended to limit the present invention in any form, and any simple amendments, equivalent changes or modifications made by those skilled in the art using the technical contents disclosed above shall all fall within the protection scope of the present invention.

What is claimed is:

1. A urine testing device, comprising:
a base;
a paper feeding module installed on the base and comprising a test paper box, a lifting mechanism, and a pushing mechanism, wherein a paper leakage groove is disposed at a bottom of the test paper box, the paper leakage groove is configured to receive a bottommost piece of test paper, which is configured to drop down by dead weight, and the lifting mechanism is configured to lift and descend the test paper box to reveal or seal the paper leakage groove;
a sample adding module installed on the base and configured to dropwise add urine to be tested on the test paper; and
a testing module installed on the base and configured to test the test paper added with the urine to obtain a urine testing result;
wherein the paper feeding module, the sample adding module, and the testing module are proximately arranged in a line moving from a first side toward a second side of the base;
wherein the pushing mechanism is configured to push out the test paper from the paper leakage groove and deliver the test paper to the sample adding module and the testing module;
wherein the base is an integrated base having a first installation area for the paper feeding module, a second installation area for the sample adding module, and a third installation area for the testing module;
wherein the first installation area is provided with a containing cavity for installing the test paper box;
wherein a paper guide table is disposed at a side of the containing cavity;
wherein a test paper translation channel on the base is disposed at a side of the paper guide table; and
wherein a bottom of the containing cavity is provided with a second groove used for embedding the paper leakage groove, and an opening of the second groove is provided with a sealing gasket for sealing the paper leakage groove.

2. A urine testing device, comprising:
a base;
a paper feeding module installed on the base and comprising a test paper box, a lifting mechanism, and a pushing mechanism, wherein a paper leakage groove is disposed at a bottom of the test paper box, the paper leakage groove is configured to receive a bottommost piece of test paper, which is configured to drop down by dead weight, and the lifting mechanism is configured to lift and descend the test paper box to reveal or seal the paper leakage groove;
a sample adding module installed on the base and configured to dropwise add urine to be tested on the test paper; and
a testing module installed on the base and configured to test the test paper added with the urine to obtain a urine testing result;
wherein the paper feeding module, the sample adding module, and the testing module are proximately arranged in a line moving from a first side toward a second side of the base;
wherein the pushing mechanism is configured to push out the test paper from the paper leakage groove and deliver the test paper to the sample adding module and the testing module;
wherein the base is an integrated base having a first installation area for the paper feeding module, a second installation area for the sample adding module, and a third installation area for the testing module; the first installation area is provided with a containing cavity for installing the test paper box; a paper guide table is disposed at a side of the containing cavity; and a test paper translation channel on the base is disposed at a side of the paper guide table;
wherein the lifting mechanism comprises:
a first motor; and
a lifting snap table that is installed in the containing cavity;
wherein the test paper box is snap-fit into the lifting snap table; and
wherein the first motor is connected to the lifting snap table and is configured to drive the lifting snap table to lift and descend, so as to drive the test paper box to lift and descend.

3. The urine testing device of claim 2, wherein the pushing mechanism comprises:
a second motor fixedly installed in a platform;
a third motor;
a pulling rod connected to the second motor; and
a screw rod connected to the third motor;
wherein the platform is sheathed on the screw rod and is internally provided with an internal thread matched with the screw rod;
wherein the platform translates along the screw rod to drive the pulling rod to translate when the third motor drives the screw rod to rotate; and
wherein the second motor is configured to drive the pulling rod between an initial position and a working position, in which the pulling rod is aligned with the paper leakage groove.

4. The urine testing device of claim 3, wherein the sample adding module comprises:
a fourth motor; and
a sample adding needle connected to a sample feeder and the fourth motor, such that the fourth motor is configured to drive the sample adding needle to move between a sample adding position and a cleaning position.

5. The urine testing device of claim 4, wherein the sample feeder comprises:
a liquid inlet tube connected to the sample adding needle; and
a plunger pump connected to a urine-collecting pipeline and a cleaning pipeline;
wherein the sample adding needle moves to the sample adding position during testing, and the plunger pump pumps the urine to be tested from the urine-collecting pipeline to the sample adding needle through the liquid inlet tube; and
wherein the sample adding needle moves to the cleaning position after testing, and the plunger pump pumps a cleaning fluid from the cleaning pipeline to the sample adding needle through the liquid inlet tube.

6. The urine testing device of claim 4, wherein the testing module comprises a photoelectric probe detector that comprises:
a support installed on the base; and
multiple sets of photoelectric probes disposed in the support in a side by side arrangement, wherein each set of photoelectric probes is configured to test one testing area on the test paper to be tested.

7. The urine testing device of claim 6, wherein the testing module further comprises:

a fifth motor connected to and configured to drive the photoelectric probe detector to move to a calibrating position, a testing position, or a test paper recycling position; and a separable test paper recycling box that is disposed below a position of the base corresponding to the test paper recycling position of the photoelectric probe detector.

8. A urine testing device, comprising:

a base;

a paper feeding module installed on the base and comprising a test paper box, a lifting mechanism, and a pushing mechanism, wherein a paper leakage groove is disposed at a bottom of the test paper box, the paper leakage groove is configured to receive a bottommost piece of test paper, which is configured to drop down by dead weight, and the lifting mechanism is configured to lift and descend the test paper box to reveal or seal the paper leakage groove;

a sample adding module installed on the base and configured to dropwise add urine to be tested on the test paper; and a testing module installed on the base and configured to test the test paper added with the urine to obtain a urine testing result;

wherein the paper feeding module, the sample adding module, and the testing module are proximately arranged in a line moving from a first side toward a second side of the base;

wherein the pushing mechanism is configured to push out the test paper from the paper leakage groove and deliver the test paper to the sample adding module and the testing module;

wherein the base is an integrated base having a first installation area for the paper feeding module, a second installation area for the sample adding module, and a third installation area for the testing module; the first installation area is provided with a containing cavity for installing the test paper box; a paper guide table is disposed at a side of the containing cavity; and a test paper translation channel on the base is disposed at a side of the paper guide table;

wherein the lifting mechanism comprises a first motor and a lifting snap table, which is installed in the containing cavity; wherein the test paper box is snap-fit into the lifting snap table; and wherein the first motor is connected to the lifting snap table and is configured to drive the lifting snap table to lift and descend, so as to drive the test paper box to lift and descend; and wherein the pushing mechanism comprises a second motor fixedly installed in a platform.

9. The urine testing device of claim 8, wherein the pushing mechanism comprises a third motor, a pulling rod operatively connected to the second motor of the pushing mechanism; and a screw rod operatively connected to the third motor; wherein the platform is sheathed on the screw rod and is internally provided with an internal thread matched with the screw rod; wherein the platform translates along the screw rod to drive the pulling rod to translate when the third motor drives the screw rod to rotate; and wherein the second motor is configured to drive the pulling rod between an initial position and a working position, in which the pulling rod is aligned with the paper leakage groove.

10. The urine testing device of claim 9, wherein the sample adding module comprises a fourth motor and a sample adding needle connected to a sample feeder and the fourth motor, such that the fourth motor is configured to drive the sample adding needle to move between a sample adding position and a cleaning position.

11. The urine testing device of claim 10, wherein the sample feeder comprises:

a liquid inlet tube connected to the sample adding needle; and a plunger pump connected to a urine-collecting pipeline and a cleaning pipeline;

wherein the sample adding needle moves to the sample adding position during testing, and the plunger pump pumps the urine to be tested from the urine-collecting pipeline to the sample adding needle through the liquid inlet tube; and wherein the sample adding needle moves to the cleaning position after testing, and the plunger pump pumps a cleaning fluid from the cleaning pipeline to the sample adding needle through the liquid inlet tube.

12. The urine testing device of claim 10, wherein the testing module comprises a photoelectric probe detector that comprises:

a support installed on the base; and multiple sets of photoelectric probes disposed in the support in a side by side arrangement, wherein each set of photoelectric probes is configured to test one testing area on the test paper to be tested.

13. The urine testing device of claim 12, wherein the testing module further comprises:

a fifth motor connected to and configured to drive the photoelectric probe detector to move to a calibrating position, a testing position, or a test paper recycling position; and a separable test paper recycling box that is disposed below a position of the base corresponding to the test paper recycling position of the photoelectric probe detector.

14. The urine testing toilet of claim 8, wherein the testing module comprises a photoelectric probe detector that comprises:

a support installed on the base;

at least one set of photoelectric probes disposed in the support, wherein each set of photoelectric probes is configured to test one testing area on the test paper to be tested;

a third motor configured to drive the photoelectric probe detector between a calibrating position, a testing position, and a test paper recycling position; and a separable test paper recycling box that is disposed in a position corresponding to the test paper recycling position of the photoelectric probe detector.

15. The urine testing device of claim 8, wherein the sample adding module comprises a third motor, a sample feeder, and a sample adding needle connected to the sample feeder and the third motor, such that the third motor is configured to move the sample adding needle between a sample adding position and a cleaning position.

16. The urine testing device smart toilet of claim 15, wherein the sample feeder comprises:

a liquid inlet tube connected to the sample adding needle; and a plunger pump connected to a urine-collecting pipeline and a cleaning pipeline;

wherein the sample adding needle moves to the sample adding position during testing, and the plunger pump pumps the urine to be tested from the urine-collecting pipeline to the sample adding needle through the liquid inlet tube; and wherein the sample adding needle moves to the cleaning position after testing, and the plunger pump pumps a cleaning fluid from the cleaning pipeline to the sample adding needle through the liquid inlet tube.

* * * * *